(12) United States Patent
Hidaka

(10) Patent No.: US 12,295,747 B2
(45) Date of Patent: May 13, 2025

(54) WEARABLE DEVICE, CONTROL METHOD FOR WEARABLE DEVICE, AND CONTROL PROGRAM FOR WEARABLE DEVICE

(71) Applicant: NEC Corporation, Tokyo (JP)

(72) Inventor: Naoya Hidaka, Tokyo (JP)

(73) Assignee: NEC CORPORATION, Tokyo (JP)

( * ) Notice: Subject to any disclaimer, the term of this patent is extended or adjusted under 35 U.S.C. 154(b) by 523 days.

(21) Appl. No.: 17/570,574

(22) Filed: Jan. 7, 2022

(65) Prior Publication Data
US 2022/0225932 A1     Jul. 21, 2022

(30) Foreign Application Priority Data

Jan. 21, 2021 (JP) ................................ 2021-007856

(51) Int. Cl.
*A61B 5/00*     (2006.01)
*A61B 5/0205*   (2006.01)
(Continued)

(52) U.S. Cl.
CPC ............ *A61B 5/681* (2013.01); *A61B 5/0205* (2013.01); *G06F 1/163* (2013.01); *H04W 4/029* (2018.02)

(58) Field of Classification Search
CPC .... A43B 3/34; A43B 3/46; A43B 3/48; A61B 5/681; A61B 5/6802; A61B 5/6801;
(Continued)

(56) References Cited

U.S. PATENT DOCUMENTS

2016/0154952 A1*  6/2016  Venkatraman ... G06Q 20/40145
                                                     726/19
2017/0160398 A1*  6/2017  Venkatraman ........ A61B 5/1112
(Continued)

FOREIGN PATENT DOCUMENTS

CN     108663701 A    10/2018
CN     110568271 A    12/2019
(Continued)

OTHER PUBLICATIONS

JP Office Action for JP Application No. 2021-007856, mailed on Jun. 4, 2024 with English Translation.
(Continued)

*Primary Examiner* — Daniel R Miller
*Assistant Examiner* — Eric Sebastian Von Wald

(57) ABSTRACT

In order to provide a wearable device that enables determining with high accuracy whether the wearable device is mounted on a living body or a fitting to be worn by a living body, the wearable device includes a base member, a receiving quality index acquisition unit, a sensor, and a transmitter. The receiving quality index acquisition unit receives a GPS signal, and acquires a receiving quality index of the GPS signal. The sensor outputs a signal depending on a positional relation of the living body and the sensor or the fitting and the sensor. The transmitter transmits the receiving quality index and the output of the sensor to a mounting determination unit. The determination unit determines whether the wearable device is mounted on the living body or the fitting, based on the receiving quality index and the output of the sensor.

12 Claims, 14 Drawing Sheets

(51) Int. Cl.
*G06F 1/16* (2006.01)
*H04W 4/029* (2018.01)

(58) Field of Classification Search
CPC ....... A61B 5/68; A61B 5/6807; A61B 5/0205;
A61B 2562/0219; A61B 5/7221; A61B
2562/0204; A61B 2562/0271; A61B
2562/029; A61B 5/1112; A61B 5/6844;
A61B 5/7264; G06F 1/163; G06F
2218/00; G06F 1/3231; G06F 1/3206;
G01C 21/165; G01R 33/072; G01S
5/0226; G01S 17/04; G01S 7/4813; G01S
11/06; G01S 19/48; G02B 27/0093;
H04W 4/029; H04W 4/02
See application file for complete search history.

(56) References Cited

U.S. PATENT DOCUMENTS

| | | | |
|---|---|---|---|
| 2017/0296124 A1 | 10/2017 | Creemers et al. | |
| 2018/0188032 A1* | 7/2018 | Ramanandan | G01S 19/52 |
| 2018/0356534 A1* | 12/2018 | Sugiyama | G01S 19/49 |
| 2019/0204838 A1* | 7/2019 | Haque | G05D 1/248 |
| 2019/0285735 A1* | 9/2019 | Hamaguchi | G01S 17/10 |
| 2020/0367827 A1* | 11/2020 | Min | G06F 3/01 |
| 2021/0118564 A1* | 4/2021 | Liu | A61B 5/316 |
| 2022/0265150 A1* | 8/2022 | De Haan | A61B 5/7207 |
| 2022/0409070 A1* | 12/2022 | Quan | A61B 5/02108 |
| 2024/0122485 A1* | 4/2024 | Farrell | A61B 5/1116 |

FOREIGN PATENT DOCUMENTS

| | | |
|---|---|---|
| CN | 110584632 A | 12/2019 |
| JP | 2014-071117 A | 4/2014 |
| JP | 5515647 B2 | 6/2014 |
| JP | 5769630 B2 | 8/2015 |
| JP | 2016-178493 A | 10/2016 |
| JP | 2017-033042 A | 2/2017 |
| JP | 2017-151995 A | 8/2017 |
| JP | 2017-182106 A | 10/2017 |
| JP | 2018-205195 A | 12/2018 |
| JP | 2019-513489 A | 5/2019 |
| JP | 6544428 B2 | 7/2019 |
| JP | 2020-000341 A | 1/2020 |

OTHER PUBLICATIONS

JP Office Communication for JP Application No. 2021-007856, mailed on Nov. 12, 2024 with English Translation.

* cited by examiner

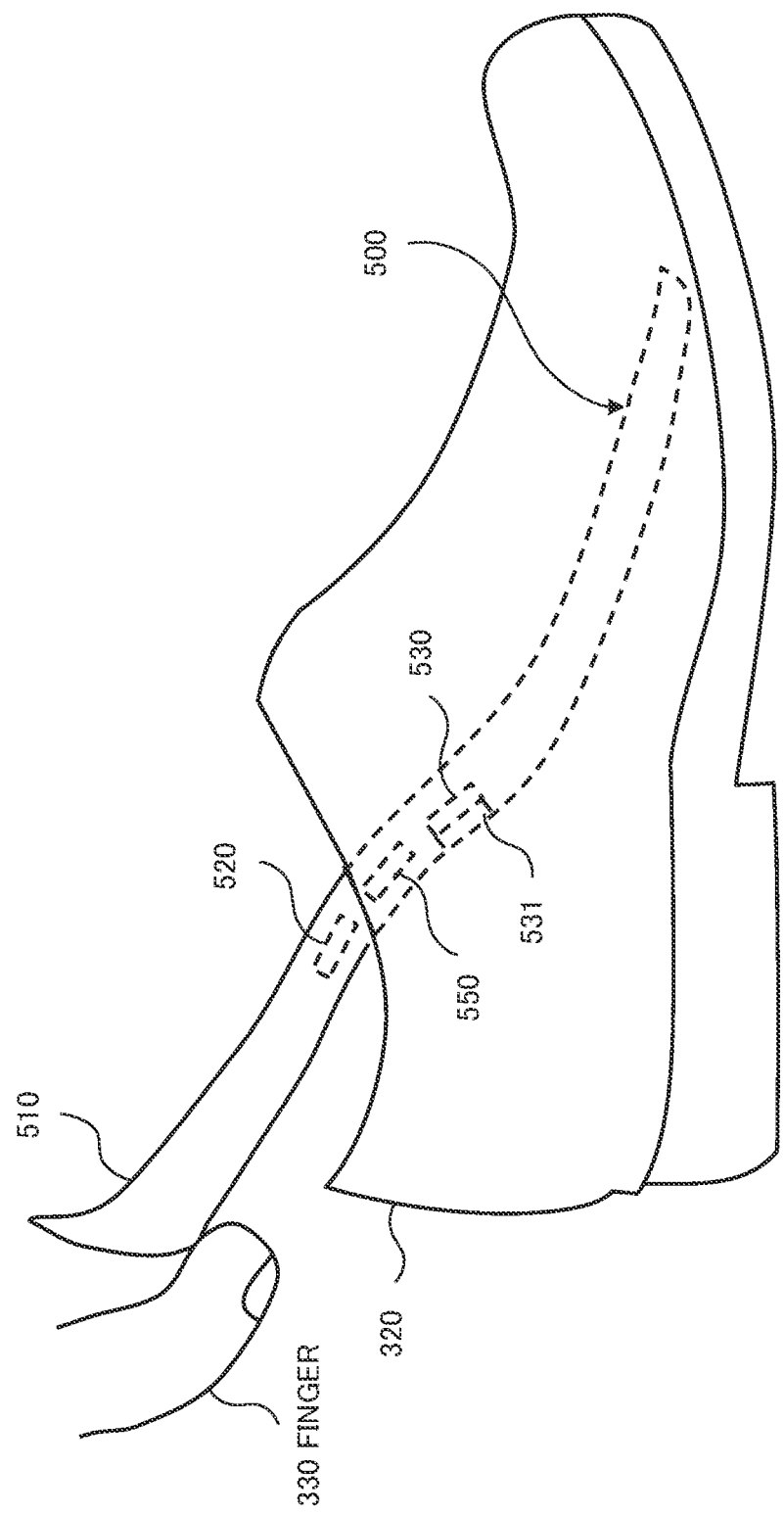

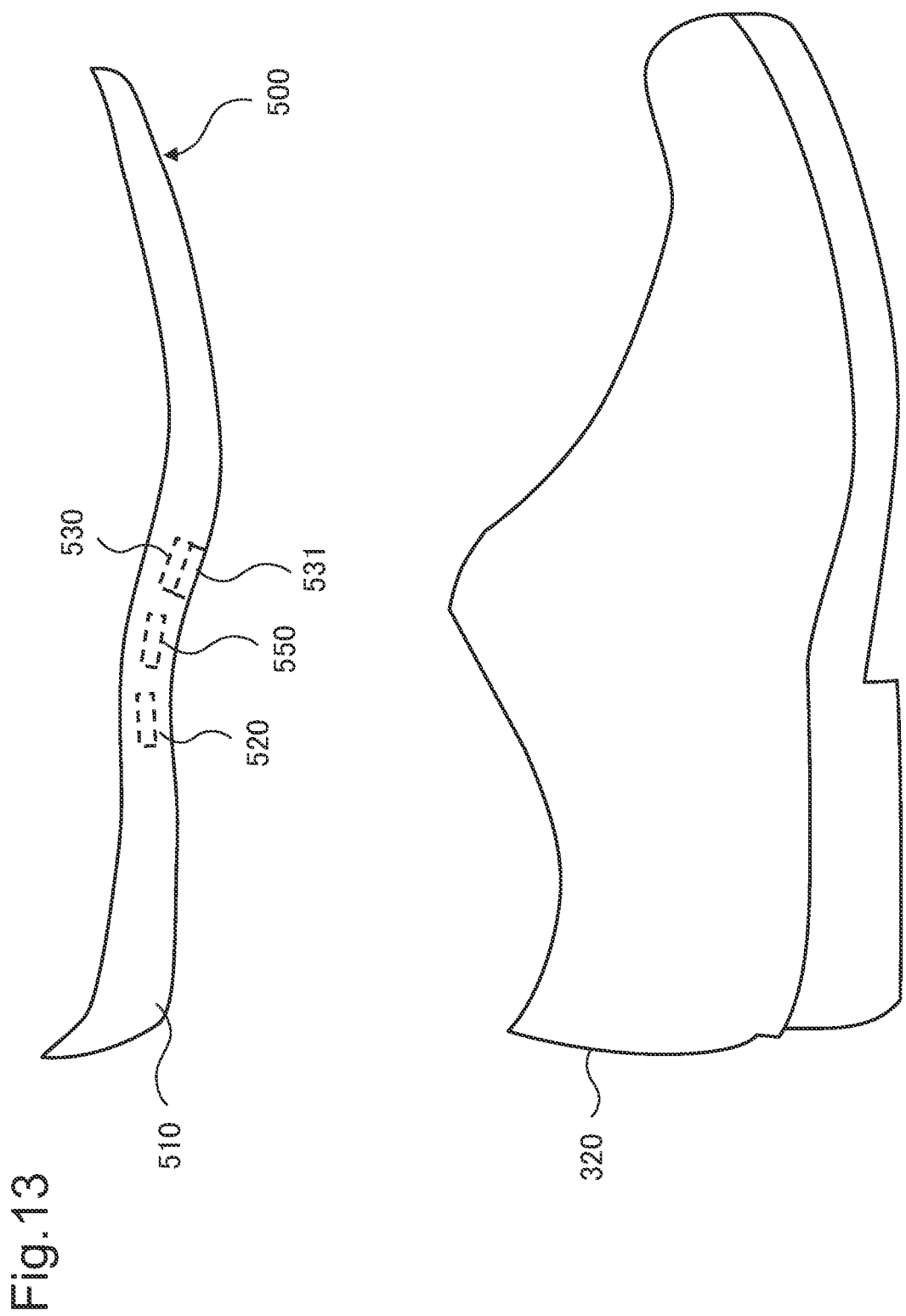

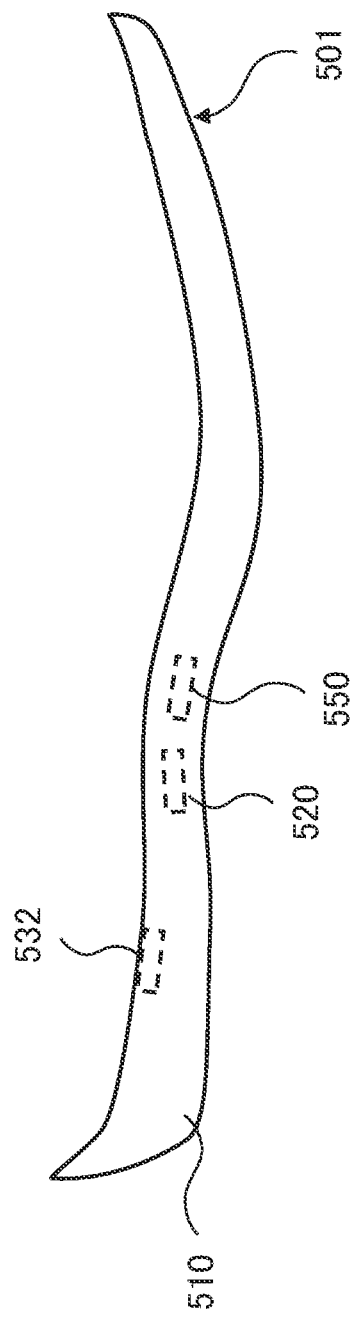

WEARABLE DEVICE, CONTROL METHOD FOR WEARABLE DEVICE, AND CONTROL PROGRAM FOR WEARABLE DEVICE

This application is based upon and claims the benefit of priority from Japanese Patent Application No. 2021-007856, filed on Jan. 21, 2021, the disclosure of which is incorporated herein in its entirety by reference.

TECHNICAL FIELD

The present invention relates to a wearable device, a control method for the wearable device, and a control program for the wearable device.

BACKGROUND ART

In recent years, an opportunity of using a wearable device for the purpose of watching over a person has been increasing. For example, it is possible to determine a location of a person to be watched over by causing the person to wear a wearable device provided with a global positioning system (GPS). However, a problem occurs that, once a person to be watched over removes a wearable device, a location of the person cannot be determined. In view of the above, an idea of providing a wearable device with a function of detecting mounting and dismounting has been proposed.

For example, PTL 1 (Japanese Unexamined Patent Application Publication No. 2017-151995) discloses a wearable terminal provided with a positioning sensor incorporated with a GPS, and a detection unit that detects whether the wearable terminal is mounted on a user. The detection unit includes an acceleration sensor or a temperature sensor. In a case where an acceleration sensor is employed, it is possible to determine that the wearable terminal is mounted when an acceleration speed is large, and it is possible to determine that the wearable terminal is not mounted when the acceleration speed is zero. Further, in a case where a temperature sensor is employed, for example, when a temperature of an arm is measured, it is possible to determine that the wearable terminal is mounted, and when the measured temperature is other than the arm temperature, it is possible to determine that the wearable terminal is not mounted.

SUMMARY

However, in the technique of PTL 1, there is a problem that erroneous detection may occur. For example, when a user (a person to be watched over) stays still, an acceleration speed of the wearable terminal becomes zero, and an error determining that the wearable terminal is not mounted may occur. Further, in a case where a temperature sensor is employed and, for example, an atmospheric temperature or a temperature of an object in contact with the wearable terminal is close to a body temperature, even when the wearable terminal is removed, there is a possibility that it is erroneously determined that the wearable terminal is mounted.

The present invention has been made in view of the above-described problem and an object of the present invention is to provide a wearable device that enables determining with high accuracy whether the wearable device is mounted on a living body or a fitting to be worn by a living body.

In order to solve the above-described problem, a wearable device according to the present invention includes: a base member to be mounted on a living body or a fitting to be worn by a living body; a receiving quality index acquisition means that is mounted on the base member, receives a GPS signal, and acquires a receiving quality index of the GPS signal; a sensor that is mounted on the base member and outputs a signal depending on a positional relation between the living body or the fitting, and the sensor itself; and a transmitting means that transmits the receiving quality index and the output of the sensor to a mounting determination means for determining whether the wearable device is mounted on the living body or the fitting, based on the receiving quality index and the output of the sensor.

Further, a control method for a wearable device according to the present invention includes, by a wearable device mounted on a living body or a fitting to be worn by a living body: receiving a GPS signal; acquiring a receiving quality index of the GPS signal; outputting, from a sensor, a signal depending on a positional relation between the living body or the fitting, and the sensor itself; and transmitting the receiving quality index and the output of the sensor to a mounting determination means for determining whether the wearable device is mounted on the living body or the fitting, based on the receiving quality index and the output of the sensor.

Further, a control program for a wearable device according to the present invention causes a wearable device mounted on a living body or a fitting to be worn by a living body to execute: processing of receiving a GPS signal; processing of acquiring a receiving quality index of the GPS signal; processing of acquiring an output from a sensor that outputs a signal depending on a positional relation between the living body or the fitting, and the sensor itself; and processing of transmitting the receiving quality index and the output of the sensor to a mounting determination means for determining whether the wearable device is mounted on the living body or the fitting, based on the receiving quality index and the output of the sensor.

BRIEF DESCRIPTION OF THE DRAWINGS

Exemplary features and advantages of the present invention will become apparent from the following detailed description when taken with the accompanying drawings in which:

FIG. 12 is a side view illustrating an operation of removing the wearable device according to the fourth example embodiment;

FIG. 13 is a side view illustrating a non-mounted state of the wearable device according to the fourth example embodiment; and FIG. 14 is a side view illustrating a modification example of the wearable device according to the fourth example embodiment.

EXAMPLE EMBODIMENT

In the following, example embodiments according to the present invention are described in detail with reference to the drawings. Although the below-described example embodiments include technically preferred limitations to implement the present invention, the example embodiments do not limit the scope of the present invention to the following. Note that, a same constituent element in each drawing is designated with a same reference sign, and description thereof may be omitted.

First Example Embodiment

Figure 1:
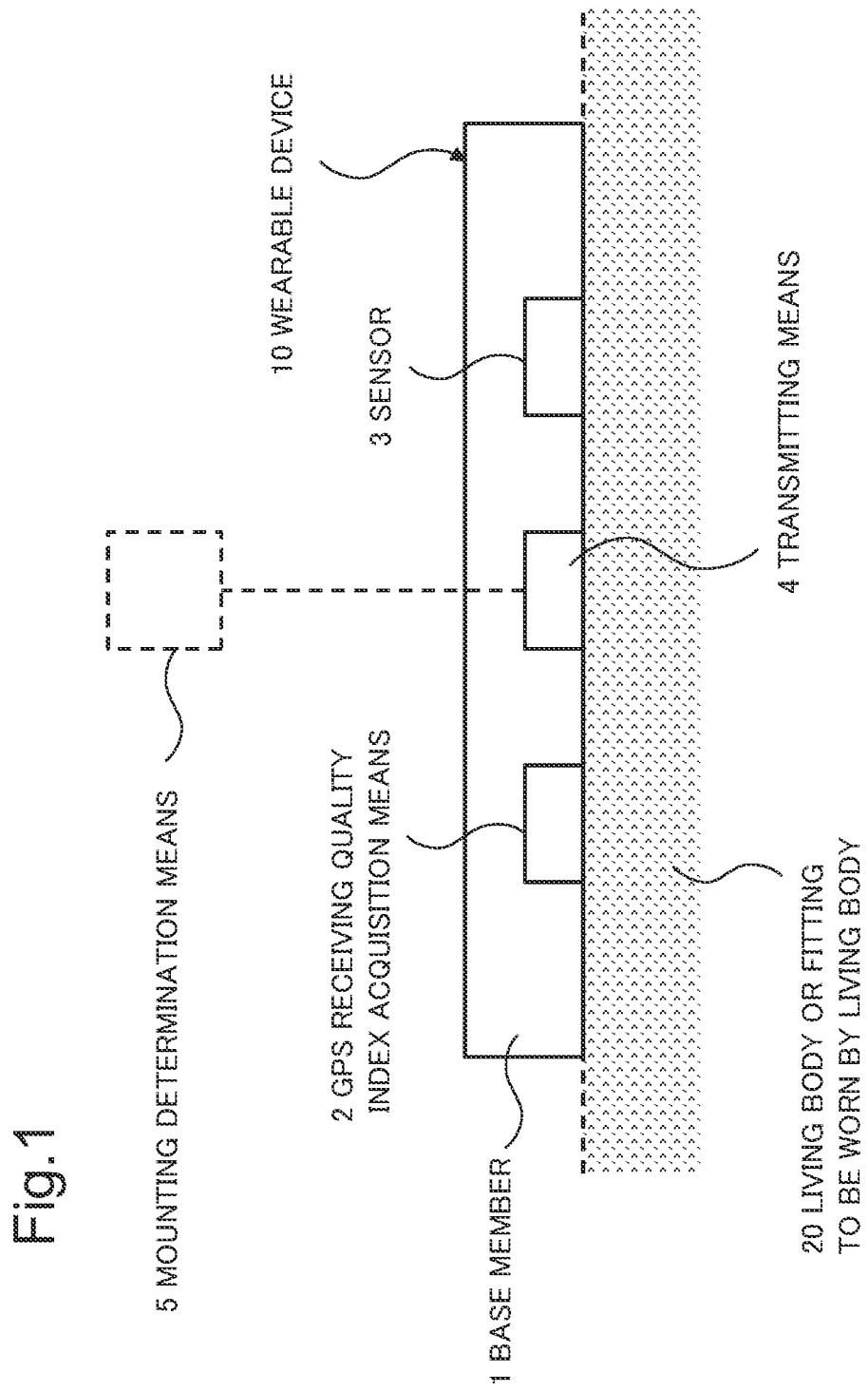
FIG. 1 is a block diagram illustrating a wearable device according to a first example embodiment.

FIG. 1 is a block diagram illustrating a wearable device 10 according to the present example embodiment. The wearable device 10 includes a base member 1, a GPS receiving quality index acquisition means 2 mounted on the base member, a sensor 3, and a transmitting means 4.

The base member 1 is a member for mounting the wearable device 10 on a living body or a fitting to be worn by a living body 20. The GPS receiving quality index acquisition means 2 receives a GPS signal, and acquires a receiving quality index of the GPS signal. As the receiving quality index, for example, it is possible to employ a carrier-to-noise ratio (CNR), or a signal-to-noise ratio (SNR). The CNR is represented by CNR=C/N, when it is assumed that electric power of a carrier wave is C, and electric power of receiving noise is N. The SNR is represented by SNR=S/N, when it is assumed that electric power of a signal is S, and electric power of receiving noise is N. Both of the CNR and the SNR indicate that the larger the CNR or the SNR, the better the quality.

The sensor 3 outputs a signal depending on a positional relation between the living body or the fitting to be worn by a living body 20, and the sensor 3. As the sensor 3, for example, a configuration is employed in which an output changes depending on a distance to a living body, such that the output decreases or increases, or a signal-to-noise ratio changes, as the sensor approaches the living body.

The transmitting means 4 transmits a receiving quality index and an output of the sensor 3 to a mounting determination means 5 for determining whether the wearable device 10 is mounted on the living body or the fitting to be worn by the living body 20, based on the receiving quality index and the output of the sensor 3.

In a case where the wearable device 10 is mounted on the living body or the fitting to be worn by the living body 20, the receiving quality index is deteriorated, since the living body blocks receiving a GPS signal. On the contrary, in a case where the wearable device 10 is not mounted on the living body or the fitting to be worn by the living body 20, the receiving quality index is improved, since a receiving state of the GPS signal is improved. In view of the above, a predetermined threshold value is set for the receiving quality index, and when the receiving quality index is larger than the predetermined threshold value, it is possible to determine that the wearable device 10 is not mounted on a living body.

Meanwhile, the receiving quality index may be deteriorated due to a factor other than that the wearable device is mounted on a living body, for example, due to a factor that a living body enters a building or enters a basement. Therefore, in a case where it is determined that the wearable device is mounted because the receiving quality index is deteriorated, erroneous determination may occur.

An output of the sensor 3 changes depending on a positional relation between the living body or the fitting to be worn by the living body 20, and the sensor 3. By setting a second threshold value for the output, and comparing the output with the second threshold value, it is possible to determine whether the wearable device 10 is mounted on the living body or the fitting to be worn by the living body 20, or removed.

Meanwhile, the output of the sensor 3 may become the same between a case where the wearable device 10 is mounted on the living body or the fitting to be worn by the living body 20, and a case where the wearable device 10 is removed. Although the condition differs depending on a type of the sensor 3. In a case where the sensor 3 is a temperature sensor, for example, there is a possibility that the wearable device 10 is determined to be mounted despite that the wearable device 10 is not actually mounted, when an outside temperature is close to a body temperature of a living body, or when the wearable device 10 is in contact with an object whose temperature is close to a body temperature of a living body.

In view of the above, the mounting determination means 5 according to the present example embodiment determines mounting and non-mounting, based on both of the receiving quality index of the GPS signal, and the output of the sensor 3. By performing determination as to mounting and non-mounting, based on a plurality of indexes having different variable factors, it is possible to lower a probability of erroneous determination.

As described above, according to the present example embodiment, it is determined whether a wearable device is mounted on a living body or a fitting to be worn by a living body, based on both of a receiving quality index of a GPS signal and an output of a sensor. Therefore, as compared with a method as disclosed in PTL 1 in which it is determined whether a wearable terminal is mounted based on only an output of a sensor, it is possible to perform determination with high accuracy.

Second Example Embodiment

The wearable device according to the first example embodiment can take various patterns to be mounted on a living body. According to the present example embodiment, a specific example employing a wristband as a base member is described.

Figure 2:
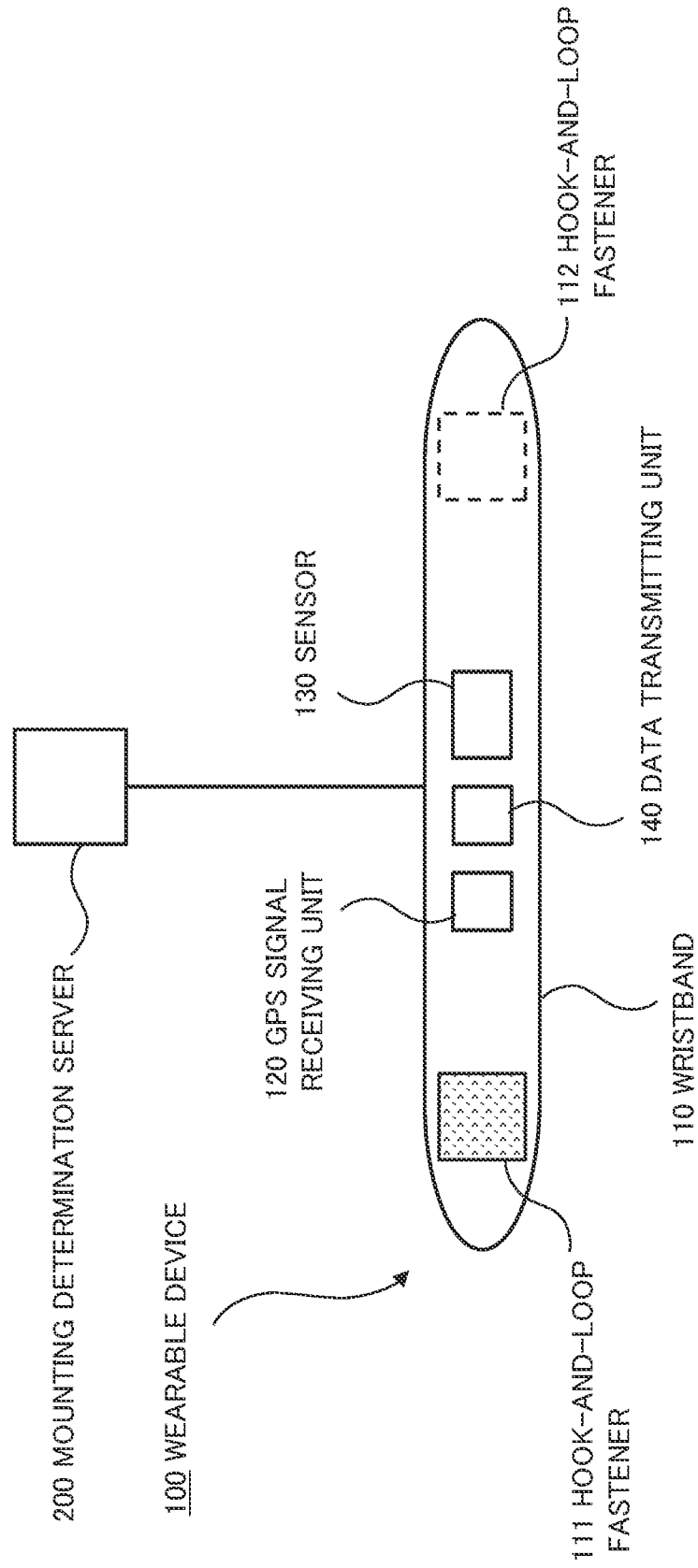
FIG. 2 is a plan view illustrating a wearable device according to a second example embodiment.

FIG. 2 is a plan view illustrating a wearable device 100 in which a GPS signal receiving unit 120, a sensor 130, and a data transmitting unit 140 are mounted on a wristband 110 as a base member. The wristband 110 is one example of the base member 1 according to the first example embodiment, the GPS signal receiving unit 120 is one example of the GPS signal receiving quality index acquisition means 2, the sensor 130 is one example of the sensor 3, and the data transmitting unit 140 is one example of the transmitting means 4. Further, a mounting determination server 200 is one example of the mounting determination means 5. A hook-and-loop fastener 111 and a hook-and-loop fastener 112 are each disposed at both ends of the wristband 110. When the wristband 110 is wound around an arm, the hook-and-loop fastener 111 and the hook-and-loop fastener 112 fix the wristband 110 on the arm by being adhesively connected to each other.

The GPS signal receiving unit 120 receives a GPS signal, and acquires a receiving signal quality index of the GPS signal. As the receiving quality index, for example, a CNR or an SNR can be employed. Note that, to simplify description, in the following description, the receiving quality index is represented by the CNR. The GPS signal receiving unit 120 may have a function of computing position information. The GPS signal receiving unit 120 can be configured as an integrated circuit having the above-described function, for example.

The sensor 130 outputs a signal depending on a positional relation between a living body (in this example, an arm) and the sensor 130 itself. As the sensor 130, for example, a configuration is employed in which an output changes depending on a distance to a living body, such that the output decreases or increases, or a signal-to-noise ratio changes, as the sensor 130 approaches the living body. Specific examples of the sensor are described later.

The data transmitting unit 140 transmits, to the mounting determination server 200, the CNR acquired by the GPS signal receiving unit 120, and the output of the sensor 130. The mounting determination server 200 is a computer including a processor, a memory, and the like, and determines whether the wearable device 100 is mounted on a living body or a fitting to be worn by a living body, based on the CNR and the output of the sensor 130. The mounting determination server 200 may have a function of determining a position of the wearable device 100 by receiving position information from the wearable device 100, or receiving GPS data from the wearable device 100.

Figure 3:
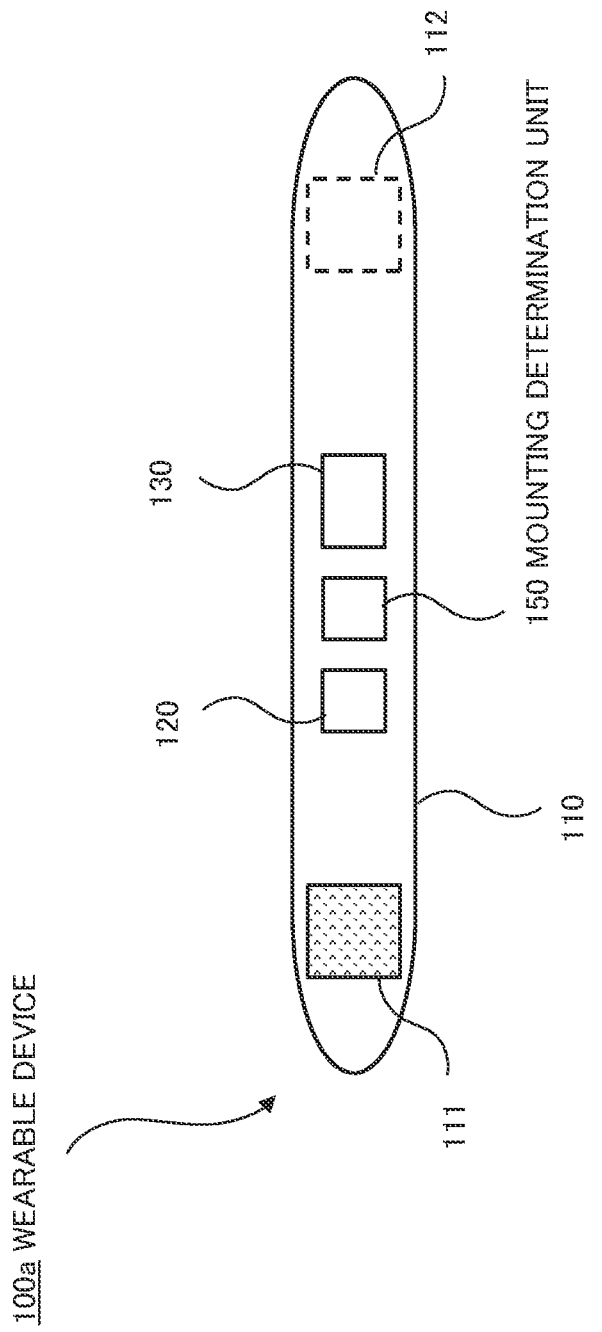
FIG. 3 is a plan view illustrating a modification example of the wearable device according to the second example embodiment.

Further, the example in FIG. 2 illustrates an example in which the mounting determination server 200 is present outside of the wearable device 100, and the data transmitting unit 140 transmits data to the mounting determination server 200. Alternatively, a mounting determination function may be configured into a chip, and the chip may be mounted in the wearable device 100. FIG. 3 is a plan view illustrating a wearable device 100a illustrating an example in which a mounting determination unit 150 as a chip is mounted in the wristband 110. As is clear from the above description, a function as a mounting determination system is the same even when the mounting determination function is provided in an external server, or even when the mounting determination function is provided in a chip mounted in the wearable device 100. Therefore, unless otherwise specifically mentioned, in the following description, description in which a mounting determination unit as a chip is employed represents both of the configurations.

Figure 4:
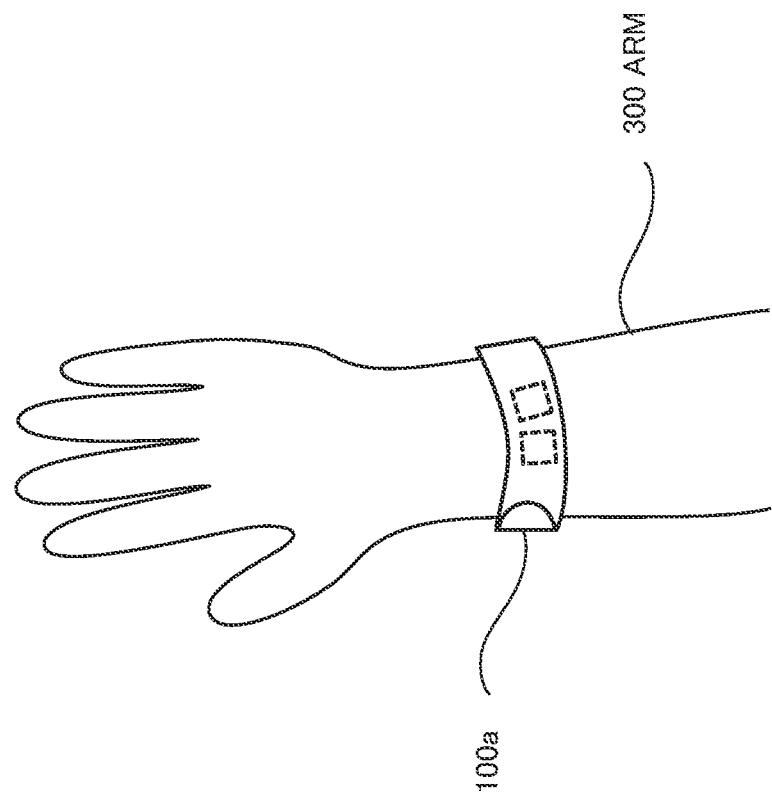
FIG. 4 is a perspective view illustrating a mounted state of the wearable device according to the second example embodiment.
Figure 5:
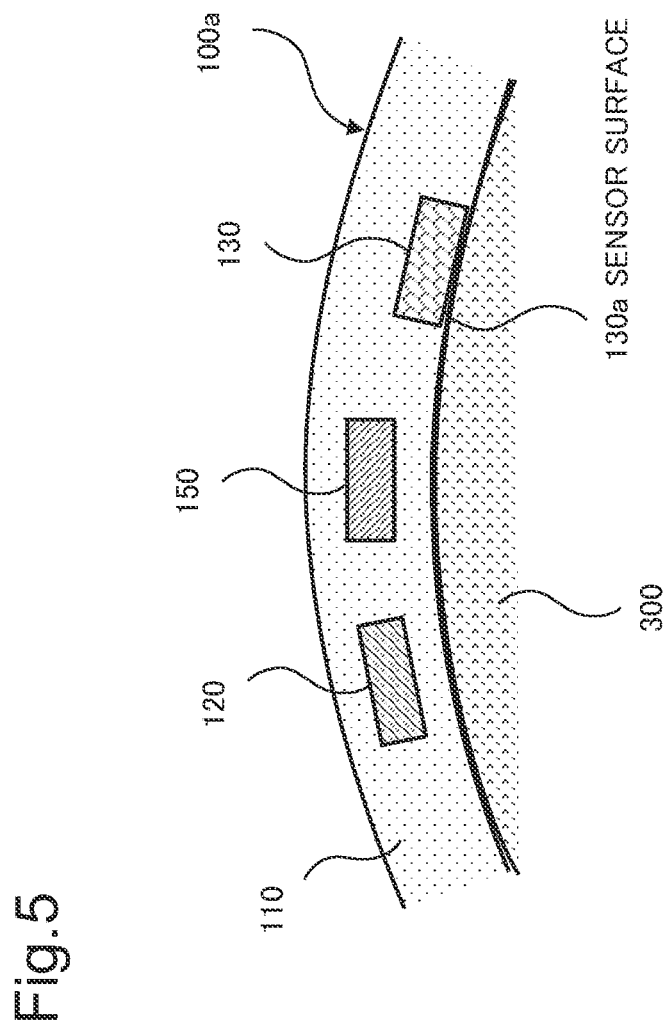
FIG. 5 is a cross-sectional view illustrating a mounted state of the wearable device according to the second example embodiment.

FIG. 4 is a perspective view illustrating an example in which the wearable device 100a of a wristband type is mounted on an arm 300. Further, FIG. 5 is a cross-sectional view illustrating a state that the wearable device 100a is wound around the arm 300. As illustrated in FIG. 5, the wristband 110 is wound around the arm in such a way that a sensor surface 130a of the sensor 130 faces the arm 300, and the wearable device 100a is fixed to the arm 300 by using the unillustrated hook-and-loop fasteners 111 and 112.

Figure 6:
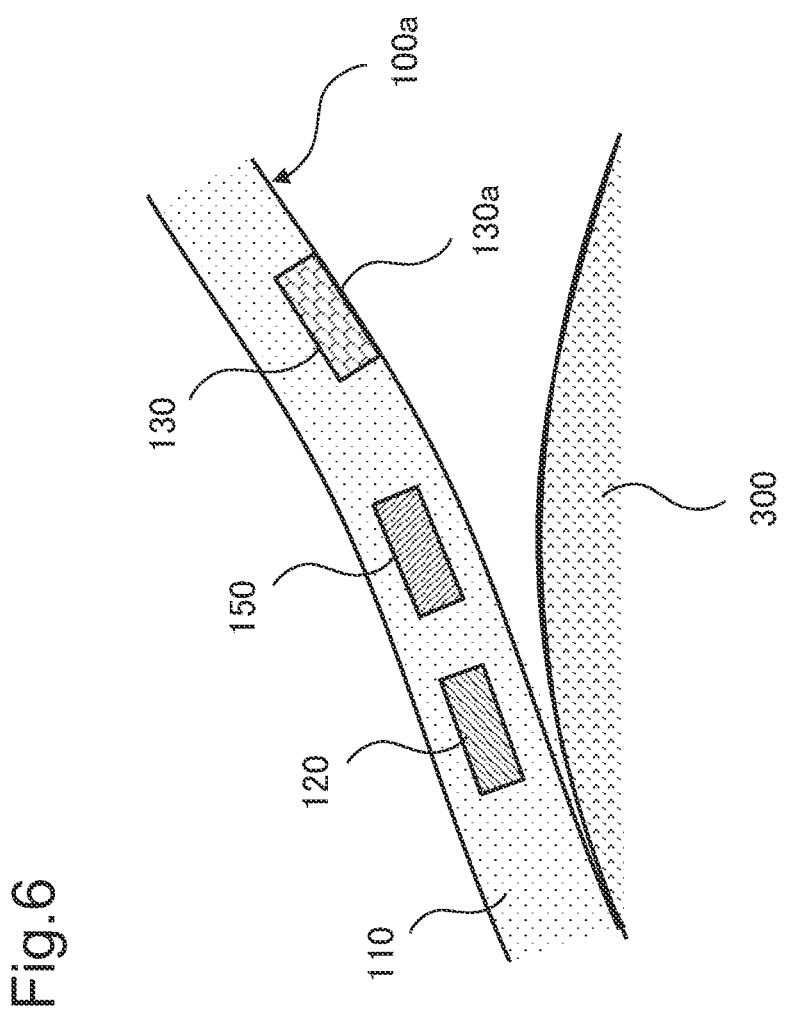
FIG. 6 is a cross-sectional view illustrating a state that the wearable device according to the second example embodiment is being removed.

FIG. 6 is a cross-sectional view illustrating a state that the wearable device 100a is being removed from the arm 300. In this state, the sensor surface 130a of the sensor 130 is away from the arm 300.

Figure 7:
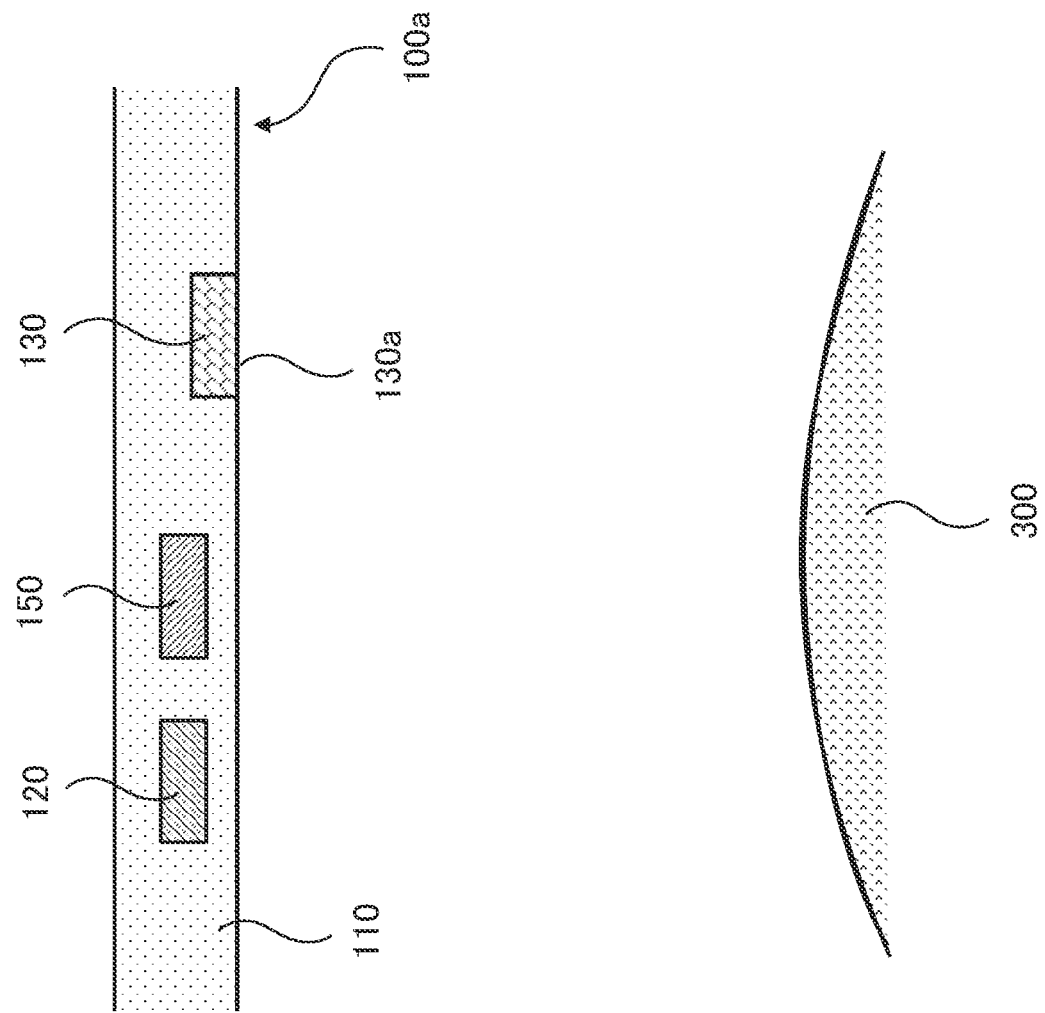
FIG. 7 is a cross-sectional view illustrating a state that the wearable device according to the second example embodiment has been removed.

FIG. 7 is a cross-sectional view illustrating a state that the wearable device 100a is completely away from the arm 300.

As the sensor 130, a configuration can be employed in which an output greatly changes between the state that the wearable device 100a in FIG. 5 is wound around the arm 300, and the state in FIG. 6 or the state in FIG. 7 in which the wearable device 100a is away from the arm 300. In the following, a mounting determination operation of the wearable device 100a is described using specific examples.

Specific Example 1

A wearable device 100a as a specific example 1 employs an illuminance sensor as the sensor 130. Note that, although the sensor 130 is referred to as the illuminance sensor in this example, the sensor 130 designates in general an optical sensor for outputting a signal depending on a light receiving amount, such as an image sensor and a luminance sensor. In a case where an illuminance sensor is employed as the sensor 130, as illustrated in FIG. 5, the wearable device 100a is mounted in such a way that the sensor surface 130a of the sensor 130 faces the arm 300. Note that, although FIG. 5 illustrates as if the sensor surface 130a firmly comes into contact with the arm 300, in a case of the illuminance sensor, a gap may be formed between the sensor surface 130a and the arm 300.

By doing so, in a case where the wearable device 100a is wound around the arm, a light receiving surface (sensor surface 130a) of the illuminance sensor faces the arm 300, and the wristband 110 covers the light receiving surface. Therefore, external light (natural light) is hardly incident on the sensor surface of the illuminance sensor, and an output of the illuminance sensor extremely decreases. Further, since the arm 300 blocks receiving a signal, the CNR acquired by the GPS signal receiving unit 120 decreases.

Meanwhile, in the state of FIG. 6 or FIG. 7, light is incident on the sensor surface 130a of the illuminance sensor, and an output increases. Further, since the GPS signal receiving unit 120 is likely to receive the GPS signal, the CNR increases.

In view of the above-described operation, by setting each threshold value for the sensor output and the CNR, for example, it is possible to determine that the wearable device is mounted when both of the sensor output and the CNR are less than the threshold values, and determine that the wearable device is in a removed state when both of the sensor output and the CNR are equal to or more than the threshold values.

Specific Example 2

A wearable device 100a as a specific example 2 employs a temperature sensor as the sensor 130. In this case, as illustrated in FIG. 5, the wearable device 100a is mounted in such a way that a temperature measuring unit of the sensor 130 comes into contact with the arm 300. By doing so, in a case where the wearable device 100a is wound around the arm, an output of the temperature sensor becomes close to a body temperature, and the CNR of the GPS signal decreases. Meanwhile, when the wearable device 100a is removed, it is often the case that the output of the temperature sensor is in a range different from a normal body temperature, and the CNR of the GPS signal increases.

As described above, in a case where an ambient temperature is close to a body temperature of a living body, the output of the temperature sensor even in the non-mounted state becomes equal to the output in the mounted state. Further, there is a case that, even in the non-mounted state, the CNR is lowered in an environment in which it is difficult to receive the GPS signal. Therefore, determining mounting and non-mounting by combining the output of the temperature sensor and the CNR enables lowering an occurrence probability of erroneous determination occurring in a case where the output of the temperature sensor and the CNR are individually employed.

For example, in a case where the wearable device 100a is actually not mounted, the output of the temperature sensor is within a predetermined range, and the CNR is equal to or more than a threshold value, it may be erroneously determined that the wearable device 100a is mounted, when the temperature sensor is employed alone. However, since the CNR is equal to or more than the threshold value, it is possible to determine that the wearable device 100a is not mounted. Further, in a case where the wearable device 100a is actually not mounted, the output of the temperature sensor is out of the predetermined range, and the CNR is less than the threshold value, it may be erroneously determined that the wearable device 100a is mounted, when the CNR is employed alone. However, since the output of the temperature sensor is out of the range, it is possible to determine that the wearable device 100a is not mounted. However, it is difficult to completely prevent erroneous determination. For example, we consider a case where the wearable device 100a is actually not mounted and the wearable device 100a is in a basement. In this case, if an ambient temperature is close to a body temperature, since the output of the temperature sensor is within the predetermined range and the CNR is less than the threshold value, it may be erroneously determined that the wearable device 100a is mounted. However, as described above, by combining the temperature sensor and the CNR, it is possible to lower a probability of erroneous determination, as compared with a case where the temperature sensor and the CNR are individually employed.

Specific Example 3

A wearable device 100a as a specific example 3 employs a humidity sensor as the sensor 130. In this case, as illustrated in FIG. 5, the wearable device 100a is mounted in such a way that a humidity measuring unit of the sensor 130 faces the arm 300. By doing so, in a case where the wearable device 100a is wound around the arm, a humidity output from the humidity sensor is high, and the CNR of the GPS signal decreases. Meanwhile, when the wearable device 100a is removed, it is often the case that the output of the humidity sensor decreases, and the CNR of the GPS signal increases.

However, in a case of humidity, an ambient humidity may become 100%. Therefore, when mounting and non-mounting are determined by the humidity sensor alone, erroneous determination is likely to occur. However, the humidity sensor can be employed as an auxiliary means. For example, in a case where the CNR is less than a threshold value, and the output of the humidity sensor is equal to or more than a threshold value, it is possible to determine that a possibility that the wearable device 100a is mounted is high.

Specific Example 4

A wearable device 100a as a specific example 4 employs an acceleration sensor or a gyro sensor as the sensor 130. In this case, the acceleration sensor or the gyro sensor is allowed to face either the arm side or the outer side. By employing the acceleration sensor or the gyro sensor, it is possible to estimate a movement of an arm from an output of the sensor. When an estimated movement matches a normal movement of a living body, a possibility that the wearable device 100a is mounted is high, and when the estimated movement is deviated from the normal movement, or the living body stays still, a possibility that the wearable device 100a is removed increases. By combining the above-described information and the CNR of the GPS signal, it is possible to determine mounting and non-mounting of the wearable device 100a with accuracy.

Specific Example 5

A wearable device 100a as a specific example 5 employs a sound sensor as the sensor 130. In this case, as illustrated in FIG. 5, the wearable device 100a is mounted in such a way that a sound measuring unit of the sensor 130 faces the arm 300. By doing so, in a case where the wearable device 100a is wound around the arm, an output of the sound sensor decreases, and the CNR of the GPS signal decreases. Meanwhile, in a case where the wearable device 100a is removed, it is often the case that the output of the sound sensor increases, and the CNR of the GPS signal increases. Therefore, it is possible to determine mounting and non-mounting of the wearable device 100a with accuracy, based on the output of the sound sensor and the CNR.

As described above, according to the present example embodiment, it is possible to determine mounting and non-mounting of a wearable device with accuracy by using the wearable device of a wristband type, and combining a CNR of a GPS signal and an output of various types of sensors.

Third Example Embodiment

Figure 8:
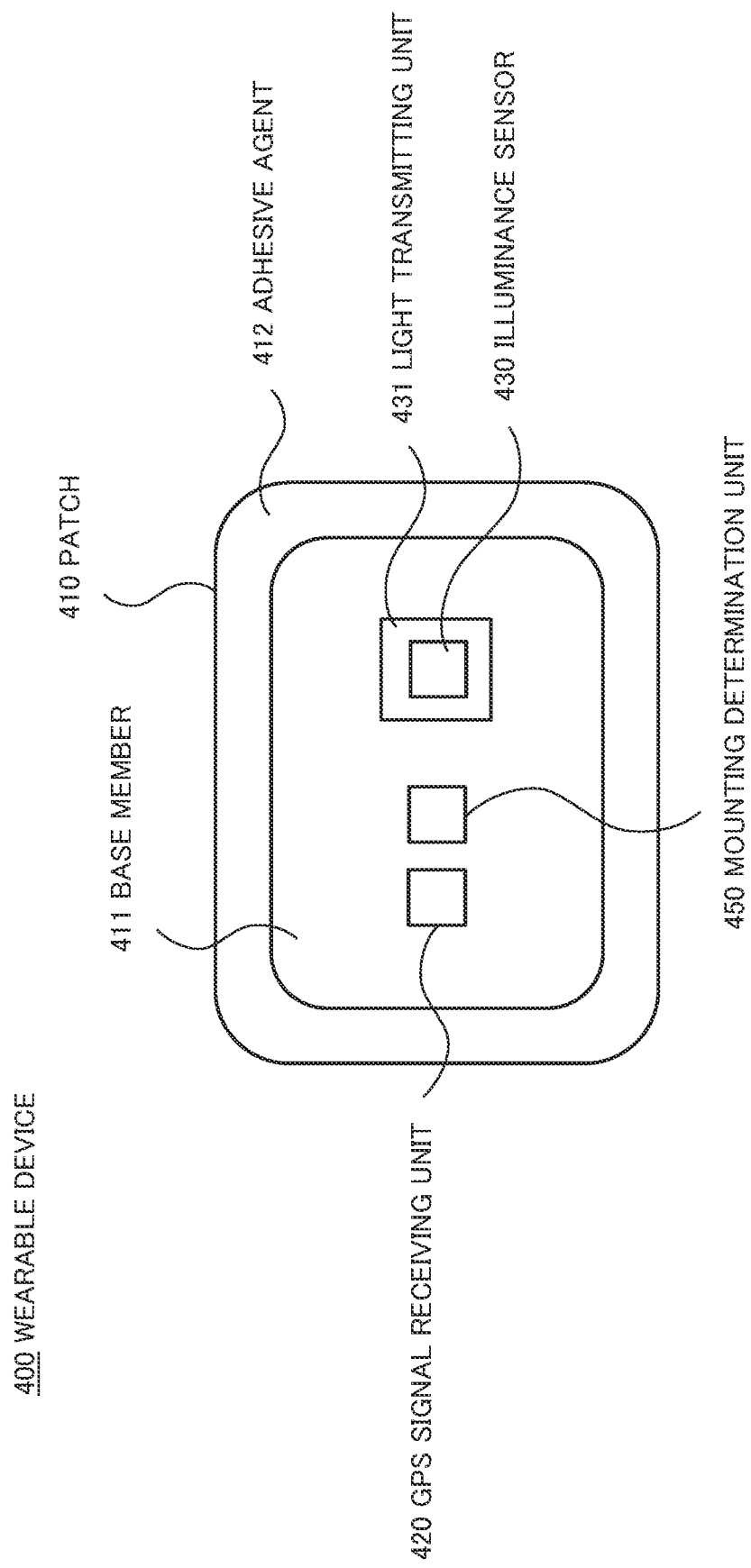
FIG. 8 is a plan view illustrating one example of a wearable device according to a third example embodiment.

According to the present example embodiment, a wearable device in which a base member is of a patch type is described. FIG. 8 is a plan view illustrating a wearable device 400 in which a GPS signal receiving unit 420, an illuminance sensor 430, and a mounting determination unit 450 are mounted on a patch 410 including a base member 411 and an adhesive agent 412. In an example of FIG. 8, the illuminance sensor 430 is employed as a sensor. The illuminance sensor 430 is disposed on a side of the base member 411 of a light transmitting unit 431 provided in the base member 411.

Figure 9:
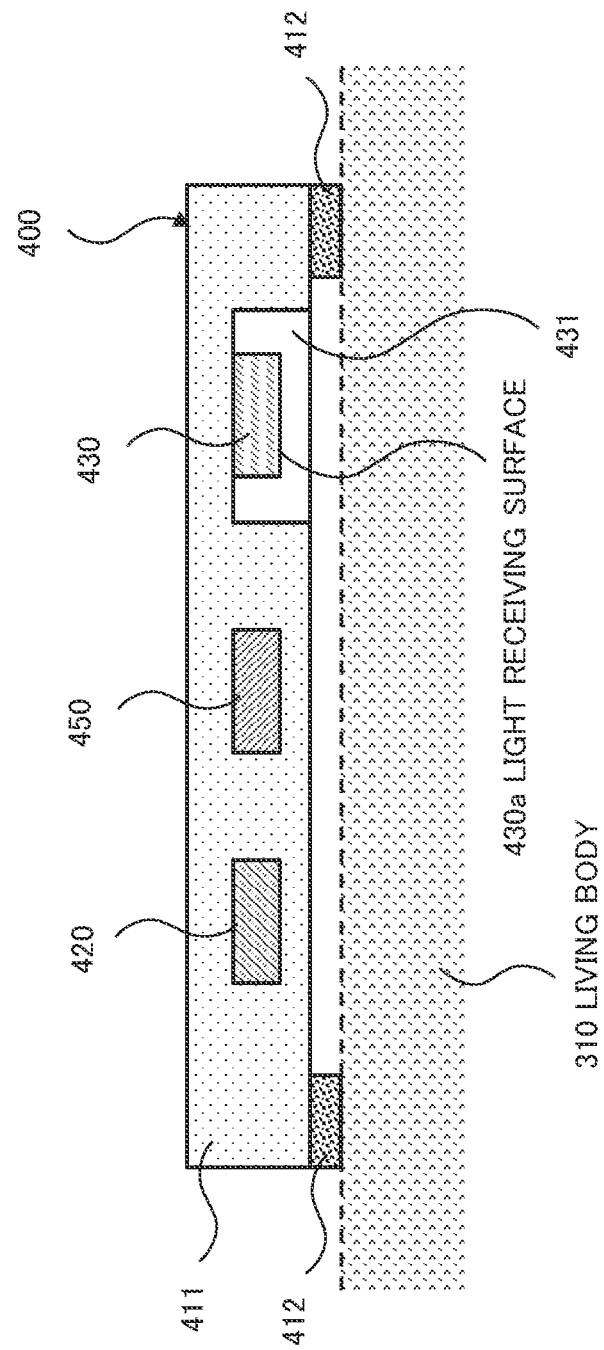
FIG. 9 is a cross-sectional view illustrating a mounted state of the wearable device according to the third example embodiment.

FIG. 9 is a cross-sectional view illustrating an example in which the wearable device 400 is mounted on a living body 310. The wearable device 400 is fixed to the living body 310 by the adhesive agent 412 in such a way that a light receiving surface 430a of the illuminance sensor 430 faces the living body 310. In this state, since the light receiving surface 430a of the illuminance sensor 430 faces the living body 310, and a periphery of the illuminance sensor 430 is surrounded by the base member 411, light is hardly incident on the light receiving surface 430a. Therefore, an output of the illuminance sensor 430 decreases. Further, since the living body 310 blocks receiving a GPS signal, a CNR output from the GPS signal receiving unit 420 decreases.

Figure 10:
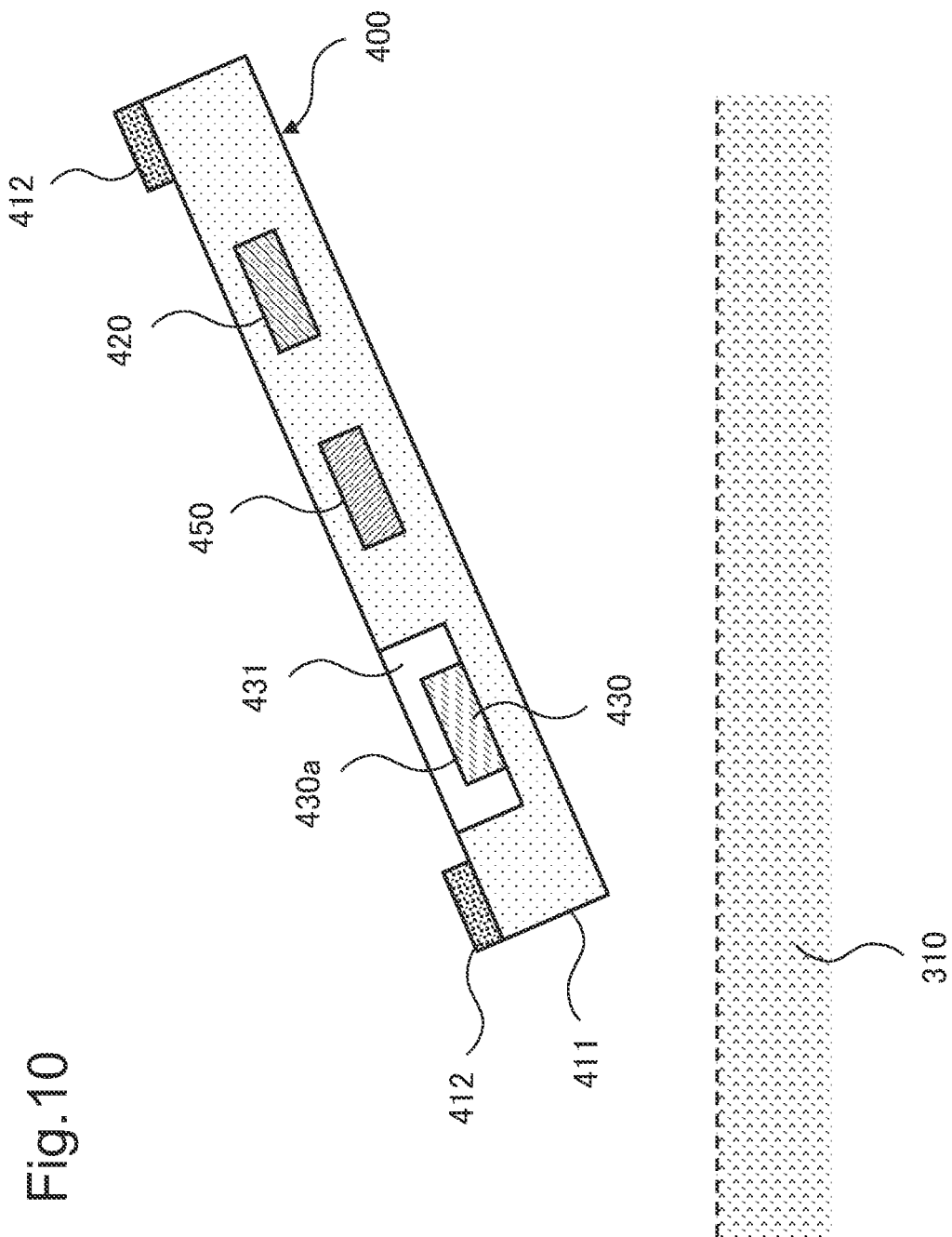
FIG. 10 is a cross-sectional view illustrating a non-mounted state of the wearable device according to the third example embodiment.

FIG. 10 is a cross-sectional view schematically illustrating a state that the wearable device 400 is removed from the living body 310. The output of the illuminance sensor 430 increases, and the CNR output from the GPS signal receiving unit 420 increases.

Note that, in the foregoing, an example is described in which an illuminance sensor is employed as a sensor. However, similarly to the second example embodiment, it is also possible to employ a temperature sensor, a humidity sensor, an acceleration sensor, a gyro sensor, or a sound sensor.

As described above, according to the present example embodiment, even in a wearable device of a patch type, it is possible to determine mounting and non-mounting of the wearable device with respect to a living body with accuracy.

Fourth Example Embodiment

Figure 11:
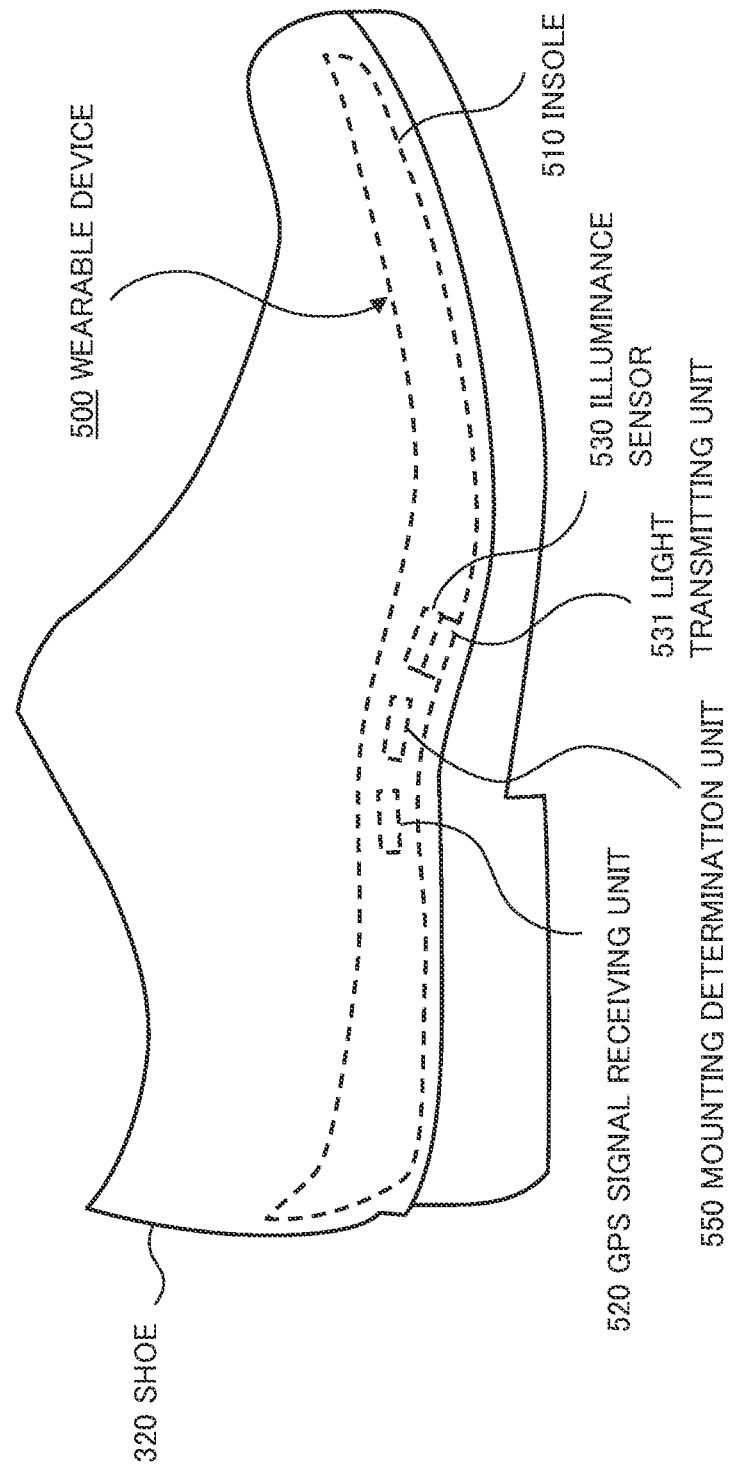
FIG. 11 is a side view illustrating a mounted state of a wearable device according to a fourth example embodiment.

According to the present example embodiment, a wearable device of an insole type in which a base member is an insole of a shoe is described. FIG. 11 is a side view illustrating a wearable device 500 in which a GPS signal receiving unit 520, an illuminance sensor 530, and a mounting determination unit 550 are mounted on an insole 510. The illuminance sensor 530 is disposed in such a way that a light receiving surface faces a bottom surface of a shoe 320. Further, a space above the light receiving surface of the illuminance sensor (a side of the bottom surface of the shoe 320) is formed into a light transmitting unit 531. The light transmitting unit 531 may be a hollow opening.

As illustrated in FIG. 11, in a case where the wearable device 500 is mounted on the bottom surface of the shoe 320, the light receiving surface of the illuminance sensor faces the bottom surface of the shoe 320 and a periphery of the illuminance sensor is surrounded by the insole 510. Therefore, external light is hardly incident on the light receiving surface. Consequently, an output of the illuminance sensor 530 decreases. Further, in a case where a user is wearing the shoe 320, a CNR output from the GPS signal receiving unit 520 decreases, and in a case where a user takes off the shoe 320, the CNR increases.

FIG. 12 is a side view illustrating that the wearable device 500 is being taken out of the shoe 320 by a finger 330. As illustrated in FIG. 12, when the wearable device 500 is moved out of the shoe 320, as the wearable device 500 is moved out, light incident on the light receiving surface of the illuminance sensor increases. Therefore, the output of the illuminance sensor 530 increases. Further, since a foot of a user is away from the GPS signal receiving unit 520, the CNR increases.

FIG. 13 is a side view schematically illustrating a state that the wearable device 500 is completely taken out of the shoe 320. In this case, since external light is incident on the light receiving surface of the illuminance sensor 530, the output increases. Further, since a foot is away from the GPS signal receiving unit 520, the CNR output from the GPS signal receiving unit 520 increases. Based on this phenomenon, it is possible to determine with accuracy whether the wearable device 500 is mounted on or taken out of the bottom surface of the shoe 320 as a fitting to be worn by a living body.

In the foregoing description, a case where the shoe 320 is not worn by a living body (user) is described. In a case of the shoe 320, there is a case that a user is wearing the shoe 320, and there is a case that a user takes off the shoe 320. In the case where a user is wearing the shoe 320, as compared with the case where a user is not wearing the shoe 320, the CNR of a GPS signal significantly decreases. Meanwhile, the output of the illuminance sensor 530 hardly changes.

In view of the above-described relation, it is possible to distinguish with accuracy the state that the wearable device 500 is mounted on the shoe 320 and a user is wearing the shoe 320, from the state that the wearable device 500 is mounted on the shoe 320 but a user takes off the shoe 320. Further, in the case where a user takes off the shoe 320, it is possible to distinguish with accuracy the case where the wearable device 500 is mounted on the shoe 320, from the state that the wearable device 500 is removed from the shoe 320.

For example, in a case where the CNR is less than a threshold value, and the output of the illuminance sensor 530 is less than a threshold value, it is determined that the wearable device is mounted. Further, in a case where the CNR is equal to or more than the threshold value, and the output of the illuminance sensor 530 is less than the threshold value, it is determined that a user takes off the shoe 320, and the wearable device 500 is mounted on the shoe 320. An example scene in which a user takes off the shoe 320 is, for example, a scene which the user is in a room where wearing shoes is strictly prohibited. In this case, taking off the shoe 320 is not abnormal.

Further, for example, in a case where the CNR is equal to or more than the threshold value, and the output of the illuminance sensor 530 is equal to or more than the threshold value, it is determined that a user takes off the shoe 320, and the wearable device 500 is removed from the shoe 320. A scene equivalent to this behavior may be, for example, a scene in which a user removes the wearable device 500 from the shoe 320 to conceal a place where the user is present. This is an abnormal behavior from a viewpoint of a watcher. The watcher can take necessary measures by detecting the abnormal behavior.

Note that, in the foregoing description, a case is described in which the illuminance sensor 530 is employed as a sensor. As the sensor, a temperature sensor, a humidity sensor, and the like can be employed. These sensors are employed to acquire information from a living body (foot of a user). Therefore, in a case where these sensors are employed, as exemplified by a wearable device 501 illustrated in FIG. 14, it is preferable to dispose a sensor 532 on an insole 510 in such a way that the sensor 532 faces a back of a foot.

As described above, according to the present example embodiment, in a wearable device of an insole type, it is possible to determine mounting and non-mounting of the wearable device with respect to a living body with accuracy. Further, it is possible to determine with accuracy whether the wearable device is mounted on or removed from a shoe.

A program causing a computer to execute processing according to the first to fourth example embodiments, and a recording medium storing the program are also included in the scope of the present invention. As the recording medium, for example, it is possible to employ a magnetic disk, a magnetic tape, an optical disc, a magneto-optical disk, a semiconductor memory, and the like.

While the invention has been particularly shown and described with reference to example embodiments thereof, the invention is not limited to these embodiments. It will be understood by those of ordinary skill in the art that various changes in form and details may be made therein without departing from the spirit and scope of the present invention as defined by the claims.

The previous description of embodiments is provided to enable a person skilled in the art to make and use the present invention. Moreover, various modifications to these example embodiments will be readily apparent to those skilled in the art, and the generic principles and specific examples defined herein may be applied to other embodiments without the use of inventive faculty.

Therefore, the present invention is not intended to be limited to the example embodiments described herein but is to be accorded the widest scope as defined by the limitations of the claims and equivalents.

Further, it is noted that the inventor's intent is to retain all equivalents of the claimed invention even if the claims are amended during prosecution.

The invention claimed is:

1. A wearable device comprising:
   a base member to be mounted on a living body or to be mounted on a fitting to be worn by a living body;
   a receiver mounted on the base member and configured to receive a GPS signal and acquire a receiving quality index of the GPS signal;
   a sensor that is mounted on the base member, and that outputs a signal depending on a positional relation of the sensor and the living body or the sensor and the fitting; and
   a transmitter transmitting the receiving quality index and an output of the sensor to a different device that is configured to determine whether the wearable device is mounted on the living body or is mounted on the fitting, based on the receiving quality index and the output of the sensor, wherein
   the receiving quality index is either a carrier-to-noise ratio or a signal-to-noise ratio, and
   when the receiving quality index becomes equal to or more than a predetermined threshold value, the different device determines that the wearable device is away from the living body.

2. The wearable device according to claim 1, wherein the different device is mounted on the base member.

3. The wearable device according to claim 1, wherein the sensor is one or a combination of an optical sensor, a temperature senor, a humidity sensor, an acceleration sensor, a gyro sensor, a sound sensor, and a displacement sensor.

4. The wearable device according to claim 3, wherein when the receiving quality index is less than the predetermined threshold value, and the output of the sensor satisfies a predetermined condition, the different device determines that the wearable device is mounted on the living body or the fitting.

5. The wearable device according to claim 3, wherein the sensor is the optical sensor, outputs a signal depending on an incident light amount, and is configured in such a way that external light incident on the optical sensor is blocked in a state that the wearable device is mounted on the fitting, and the optical sensor is mounted on the fitting,
   when the receiving quality index is equal to or more than the predetermined threshold value, and a light amount detected by the optical sensor is equal to or more than a predetermined second threshold value, the different device determines that the wearable device is not mounted on the living body, and is also removed from the fitting, and,
   when the receiving quality index is equal to or more than the predetermined threshold value, and a light amount detected by the optical sensor is less than the predetermined second threshold value, the different device determines that the wearable device is not mounted on the living body, but is mounted on the fitting.

6. The wearable device according to claim 5, wherein when the receiving quality index is less than the predetermined threshold value, and a light amount detected by the optical sensor is less than the predetermined second threshold value, the different device determines that the wearable device is mounted on the living body, and the fitting is mounted on the living body.

7. The wearable device according to claim 2, wherein the sensor is one or a combination of an optical sensor, a temperature senor, a humidity sensor, an acceleration sensor, a gyro sensor, a sound sensor, and a displacement sensor.

8. The wearable device according to claim 7, wherein when the receiving quality index is less than the predetermined threshold value, and the output of the sensor satisfies a predetermined condition, the different device determines that the wearable device is mounted on the living body or the fitting.

9. The wearable device according to claim 4, wherein the sensor is the optical sensor, outputs a signal depending on an incident light amount, and is configured in such a way that external light incident on the optical sensor is blocked in a state that the wearable device is mounted on the fitting, and the optical sensor is mounted on the fitting,
   when the receiving quality index is equal to or more than the predetermined threshold value, and a light amount detected by the optical sensor is equal to or more than a predetermined second threshold value, the different device determines that the wearable device is not mounted on the living body, and is also removed from the fitting, and,
   when the receiving quality index is equal to or more than the predetermined threshold value, and a light amount detected by the optical sensor is less than the predetermined second threshold value, the different device determines that the wearable device is not mounted on the living body, but is mounted on the fitting.

10. The wearable device according to claim 9, wherein when the receiving quality index is less than the predetermined threshold value, and a light amount detected by the optical sensor is less than the predetermined second threshold value, the different device determines that the wearable device is mounted on the living body, and the fitting is mounted on the living body.

11. A control method for a wearable device to be mounted on a living body or to be mounted on a fitting to be worn by a living body, the control method comprising:
    receiving, by the wearable device, a GPS signal;
    acquiring, by the wearable device, a receiving quality index of the GPS signal;
    outputting, by the wearable device and from a sensor, a signal depending on a positional relation between the living body or the fitting, and the sensor;
    transmitting, by the wearable device, the receiving quality index and an output of the sensor to a different device configured to determine whether the wearable device is mounted on the living body or the fitting, based on the receiving quality index and the output of the sensor;
    determining, by the different device, that the receiving quality index becomes equal to or more than a predetermined threshold value; and
    determining, by the different device, that the wearable device is away from the living body,
    wherein the receiving quality index is either a carrier-to-noise ratio or a signal-to-noise ratio.

12. A non-transitory computer-readable storage medium storing a control program executable by a wearable device to perform processing, the wearable device to be mounted on a living body or a fitting to be worn by a living body, the processing comprising:

receiving a GPS signal;
acquiring a receiving quality index of the GPS signal;
acquiring an output from a sensor that outputs a signal depending on a positional relation between the living body or the fitting, and the sensor; and
transmitting the receiving quality index and an output of the sensor to a different device configured to determine whether the wearable device is mounted on the living body or the fitting, based on the receiving quality index and the output of the sensor, wherein
the receiving quality index is either a carrier-to-noise ratio or a signal-to-noise ratio, and
when the receiving quality index becomes equal to or more than a predetermined threshold value, the different device determines that the wearable device is away from the living body.

* * * * *